United States Patent [19]

Weissman

[11] Patent Number: 5,326,263

[45] Date of Patent: Jul. 5, 1994

[54] LIGHT-CURABLE TOOTH REINFORCEMENT

[76] Inventor: Bernard Weissman, 225 E. 48th St., New York, N.Y. 10017

[21] Appl. No.: 898,769

[22] Filed: Jun. 12, 1992

[51] Int. Cl.$^5$ ............................ A61C 5/02; A61C 5/08
[52] U.S. Cl. .................................... 433/224; 433/225; 433/220; 433/221
[58] Field of Search ............... 433/218, 219, 220, 221, 433/224, 225, 226, 215

[56] References Cited

U.S. PATENT DOCUMENTS

| | | | |
|---|---|---|---|
| 4,622,012 | 11/1986 | Smoler | 433/221 |
| 4,631,030 | 12/1986 | von Weissenfluh | 433/149 |
| 4,696,646 | 9/1987 | Maitland | 433/149 |
| 4,726,770 | 2/1988 | Kurer | 433/215 X |
| 4,759,714 | 7/1988 | Szegvary | 433/221 |
| 5,030,093 | 7/1991 | Mitnick | 433/215 X |
| 5,073,112 | 12/1991 | Weil | 433/224 X |
| 5,088,927 | 2/1992 | Lee | 433/224 |
| 5,092,773 | 3/1992 | Levy | 433/224 |
| 5,116,227 | 5/1992 | Levy | 433/224 X |
| 5,165,893 | 11/1992 | Thompson | 433/224 |

FOREIGN PATENT DOCUMENTS

| | | | |
|---|---|---|---|
| 3411366 | 10/1985 | Fed. Rep. of Germany | 433/215 |
| 2645431 | 10/1990 | France | 433/224 |
| 0669514 | 3/1989 | Sweden | 433/149 |
| 91/07142 | 5/1991 | World Int. Prop. O. | 433/225 |

Primary Examiner—Gene Mancene
Assistant Examiner—Nicholas D. Lucchesi
Attorney, Agent, or Firm—Barry G. Magidoff; Paul J. Sutton

[57] ABSTRACT

There is provided a procedure to maintain an otherwise whole tooth, from which the nerve has been removed by carrying out a procedure which includes inserting a thin flexible post, preferably formed of a light-transmitting, physiologically inert material, to the full depth of a prepared relatively narrow tooth nerve canal, which has previously been sealed at its bottom with gutta percha. The post is permitted to abut against the gutta percha. The post is then surrounded by a film of a composite-filler or sealant, which is preferably light-curable, coating the post while supporting and sealing the walls of the canal. The post is sufficiently flexible as to be able to follow the curvature of the canal, which may retain a slight natural curvature. The composite filler or sealant is then cured, preferably by an optical radiation carried through the preferably transparent post. In one embodiment the light-curing post is removable after the sealant has been at least partially cured. There is also provided a post formed of a light-transmitting flexible material, the post comprising a substantially cylindrical shank portion and an inwardly tapering, or convergent, first end.

12 Claims, 9 Drawing Sheets

LIGHT-CURABLE TOOTH REINFORCEMENT

BACKGROUND OF THE INVENTION

The present invention relates to a method for strengthening a tooth and root from which the nerve has been removed, and to a dental post which is formed of a relatively soft and plastic polymer, and which is preferably light-transmitting, and can provide centering for the forming of a bracing filler to reinforce internally the walls of pulpless roots while providing for access to the canal in endodontic retreatment procedures.

It is well known art in the dental field to remove an injured nerve, and fill the root apex with gutta percha, preparatory to other reconstructive procedures, including filling the canal with a hard cement material. It is also common, where the coronal part of the tooth is missing or severely damaged, to grind away the diseased remaining upper surface of the tooth so as to provide an appropriate form for a dental prosthesis to be anchored to the tooth via a cast metal anchor extending into the widened root canal. Such dental anchors are generally cemented into the bore hole, or may be held by screw-threads, and in some cases the anchors are provided with textured or undulating lateral surfaces to further assist in securing the anchor to the cement. It has been found, however, that the strength of the repaired tooth, or the security of the dental prosthesis, may be compromised by a severely enlarged canal, with thin remaining walls; in such condition the root may not be sufficiently strong to support a prosthesis, even where the root was firmly anchored in the jaw bone.

Presently, such problems when found in roots with flared and wide canals and with thin, unsupported walls, require further widening and reshaping of the canal to form a continuous straight internal surface, and then filling the space with custom shaped cast metal posts with an extending core foundation above the root for attaching a coronal replacement. However, the difficulties created by the bulky metal post surrounded by thin walled roots are often the cause of split roots requiring the extracting of its fragments and a replacement with costlier implants and prosthetic devices. Another objection and difficulty with metal cast posts, is the unavoidable metal shadow transmitted through the thin root walls and their surrounding soft tissues, which is an impairment to achieving esthetic results, especially in the visible anterior (front) teeth. Further, such individually fashioned cast posts add additional cost, and require a greater number of costly office visits by the patient.

It was also known to use pins, or posts, formed from polymeric plastics, for the formation of dental fixtures, for example, by casting by the 'lost wax' process. Such prior pins or posts were not used in the patient's mouth and were generally opaque.

SUMMARY OF THE INVENTION

Accordingly, it is an object of the present invention to provide a method for strengthening a root and tooth from which the nerve has been removed, while preserving the opportunity for relatively easy access to the interior of the tooth for retreatment. It is a further object of this invention to provide a method for strengthening the root, and the coronal part, in a tooth having an excessively large, flared canal, after the removal of an injured nerve, and to enhance the ability of the tooth to withstand a higher impact in functional and parafunctional masticatory movements, permanently and during continued clinical treatment of an infected tooth. It is yet another object of the present invention to provide a resilient dental post and reinforcing element formed of a light-transmitting material, with a light-curable composite filler to carry out this method.

These and other objects are achieved in accordance with the present invention as follows: First, to maintain an otherwise whole tooth, especially in young people, from which the nerve has been removed by usual means without significantly widening or straightening the canal, the apex of the canal is sealed with, e.g., gutta percha. A thin flexible post, formed of a light-transmitting, physiologically inert (e.g., FDA-approved) material, is inserted to the full depth of the prepared, relatively narrow canal, until the post abuts against the gutta percha, and is preferably surrounded by a film of a composite-filler or sealant, which is most preferably light-curable, thus coating the post while supporting and sealing the walls of the canal. The cured composite acts as a casement-sealant for the inner dentin walls of the canal, protecting it against leakage and deterioration.

The post is coated with sufficient curable composite sealant material to seal the walls of the root and to secure the post in the canal; the post is sufficiently flexible, that it can follow the curvature when entering the canal, which in this embodiment of the invention may retain a slight natural curvature.

The composite-filler casement and sealant is preferably cured by light carried by trans-illumination through the entire length and circumference of the transparent plastic post, and after the composite is cured the length of the post is reduced to allow ample space to securely cover and to also seal the entry opening, through the crown of the tooth, created during the procedure of accessing the canal. Such procedures are most often performed in the younger population, with traumatic injuries caused by accidents, which require an interim solution until the full growth and development of the young person, at about the age of 16–18, or even older. The encapsulated and sealed plastic post, with its surrounding composite casement, liner and sealant, strengthens the pulpless root, precludes leaching of color from the presently used gutta percha, and provides future access for future work, such as replacement of the plastic post with a stronger metal post, if necessary.

In the second embodiment of this invention where the tooth is broken or otherwise impaired, after the nerve is removed, the canal is widened to remove all potentially infected material, leaving only sound tooth and root structure, and an appropriate size canal is created by using a dental forming or reamer tool. With the present invention, it is possible to provide adequate support and anchorage in healthy embedded roots, even in cases with very thin, unsupported walls. In the past, such thin walled root structures had a poor prognosis in spite of the fact that the root was firmly anchored in the jawbone. In accordance with this invention, roots with thin walls can be braced, reinforced and soundly repaired to sufficiently support single or multiple coronal prosthetic replacements while providing in the remodeled structure, future access to the canal when endodontic retreatment is required.

In a third embodiment of this invention, the plastic curing post is used to form a casement sealer in a tooth canal during medical treatment of a diseased tooth. After a canal has been reamed out and a nerve removed it is often necessary to have an extended period of treatment, often lasting for several months. During this period of treatment the tooth canal must remain open for continuing administration of medication, but recognizing that at least a temporary enclosure must be made to prevent particles from entering the canal. In previous situations, there would almost always be significant leakage into the canal with resultant degradation of the interior walls of dentin. Using the present invention, it is now possible to form a casement-sealant along the entire inner surface of the canal, surrounding the post, which post can be readily removed for the insertion of medication and then replaced to close up the canal. In this situation, even if there is leakage into the canal the casement sealant protects the dentin from degradation and thus obviates further widening of the canal to remove degraded dentin is avoided. It must be noted, of course, that during the period of extended medical treatment, there is no gutta percha in the apex of the canal, so as not to interfere with the flow of medication to the bone structure.

When preparing the canal, a reamer is selected having a specific convergent contour on its forming end. The innermost end of the bored out hole thus tapers to a minimum predetermined profile and diameter. This can be readily achieved by utilizing a dental reamer tool, i.e., one which provides a drilling end portion tapering longitudinally axially endwardly to a minimum effective diameter, and providing an axially facing drill-cutting surface for boring out the tooth. At the end of the drilling tool closest to the powered end section, there also can be provided a divergent, towards the end tapered counter-bore drilling section, which can form an enlarged bore diameter at the outer end of the bored out canal. Such a divergent end is primarily useful for removing relatively large quantities of diseased tissue.

After the root canal has been cleaned, and any infection or disease is treated, the canal apex is sealed with gutta percha, and a reamer of specific size is used to form a centering position at the lower end of the canal, removing any excess gutta percha; and a matching size plastic, preferably trans-illuminating post, is placed into the canal and centered therein. The post preferably comprises a generally cylindrical shank and convergent end portion; the shank diameter is preferably smaller than that of the canal to provide space for the application of a curable composite for resurfacing and sealing the inner walls of the canal. The convergent post end portion tapers longitudinally endwardly to a minimum effective diameter at the innermost end, and preferably has a profile matching the drill or reamer tool end, thus allowing it to seat into the formed innermost end portion of the canal, cradled by the gutta percha at the innermost end. A marker is placed at the outer end of the curing post and is lined up with the plane of the root canal entrance, as a reference for reseating the post after the post is temporarily withdrawn from the canal for the emplacement of curable composite material.

Preferably, light-curable composite is introduced into the canal in sufficient quantity to fill the void in the root once the post is reseated, and the post is then pressed back into the canal, being immersed in the composite to its full depth up to the level of the marker. The post is now set fully into position, contacting the gutta percha, if present, in the lower, converging portion of the prepared canal, and closely spaced from the root walls immediately above the apex, with a thin line of composite sealant forming an annulus between the post and the walls, which had been drilled out to the proper profile by the corresponding dental reamer. An easily removed material fills the apex, to prevent blockage by the cured composite, permitting medication to be administered through the apex, and to be replaced with gutta percha when a permanent closing is to be accomplished.

After the post is fully seated in the convergent inner end of the canal, and a light-curable composite material is in place in the canal and surrounding the post, a light beam is directed over the post outer end trans-illuminating the post and being radiated out from the post end and circumference into the canal, thus curing the surrounding curable composite material fully along its entire length and surrounding circumference.

Preferably, the post is also provided with a central channel and a relatively thin rod slidably held within the channel; the rod may extend at least into the convergent, or bullet-shaped end, and can have a reflective internal end. In this preferred embodiment, the thin rod is an optical glass fiber, or may be formed of a variety of other light-transmitting substances, extending through the central channel through its entire length and beyond and thus serves to provide a more efficient transmission of light into and throughout the post, and into the apex of the root.

After the composite has been cured, subsequent treatment can follow several paths: First, as explained above, when dealing with a youthful patient, and an otherwise healthy and whole tooth, the plastic post can be cut down, so that it is wholly immersed in the tooth canal, and the coronal opening closed and sealed. Alternatively, the plastic post can be replaced by installation of a stronger prefabricated metal post, that may serve as an anchor and support for prosthetic replacement restorations.

In a most preferred embodiment, the initial plastic post described above, has a substantially smooth circumferential surface, along the portion inserted into the canal, so that it can be more readily removed by simply being gently twisted and pulled out. The thus removed smooth post can be replaced with either another plastic post or with a metal post; the replacement plastic post should have a circumferential surface which is intermittently grooved; the grooves are preferably circumferential so as to serve to help retain the post in the canal. In addition, it has been found that the grooves enhance the light curing illumination radiated from the post to the light-curable composite filler, thus permitting the quicker and more complete curing of the cement, as the grooved post is slowly pressed into the canal; the grooved post is preferably slightly smaller in diameter than the first smooth post, which permits ready admission into the original channel left by the smooth post, and also permits the application of a fresh layer of cement to secure the grooved post in place, after the original cement composite has been fully cured. The enhanced trans-illumination of light along the entire length and circumference of the post, fully cures the surrounding composite material in the innermost reaches of the canal and into the apex. The grooved post which cannot readily be twisted and pulled out, can be drilled out safely with the same size reamer, leaving a precisely sized channel for any needed retreatment.

It has further been found that the rounded, convergent tip of the post of this invention enhances the trans-illuminating effectiveness of the post; the greatest intensity and concentration of trans-illuminated light occurs at the most convergent tip curvature of the cone-shaped inner end of the post. This phenomenon can be most advantageously used after the composite is initially cured as described above; the smooth post can be removed by twisting it, and pulling it out as explained above; the smooth post is preferably replaced with a grooved post of a slightly smaller diameter, which is slowly pushed into, or intermittently moved along, the entire length of the canal, for example, in 3–4 incremental depth movements, each for the duration of some seconds, which would provide maximum assurance of fully curing the composite material along its entire length, regardless of the thickness of the composite. Alternatively, if the post cannot be pulled out, the initial smooth post can be reamed out using the appropriate size reamer, and the new slightly smaller grooved post could be slowly or intermittently reinserted, as described above, connected to the light source so as to concentrate the light as much as possible.

Further details of the present invention are shown in the accompanying drawings, by way of example and not by way of exclusion. Many portions of the invention or the context therefor are shown in schematic representation, where greater detail is unnecessary as it will be apparent or well-known to those skilled in the art. Referring to the accompanying drawings.

Figure 1:
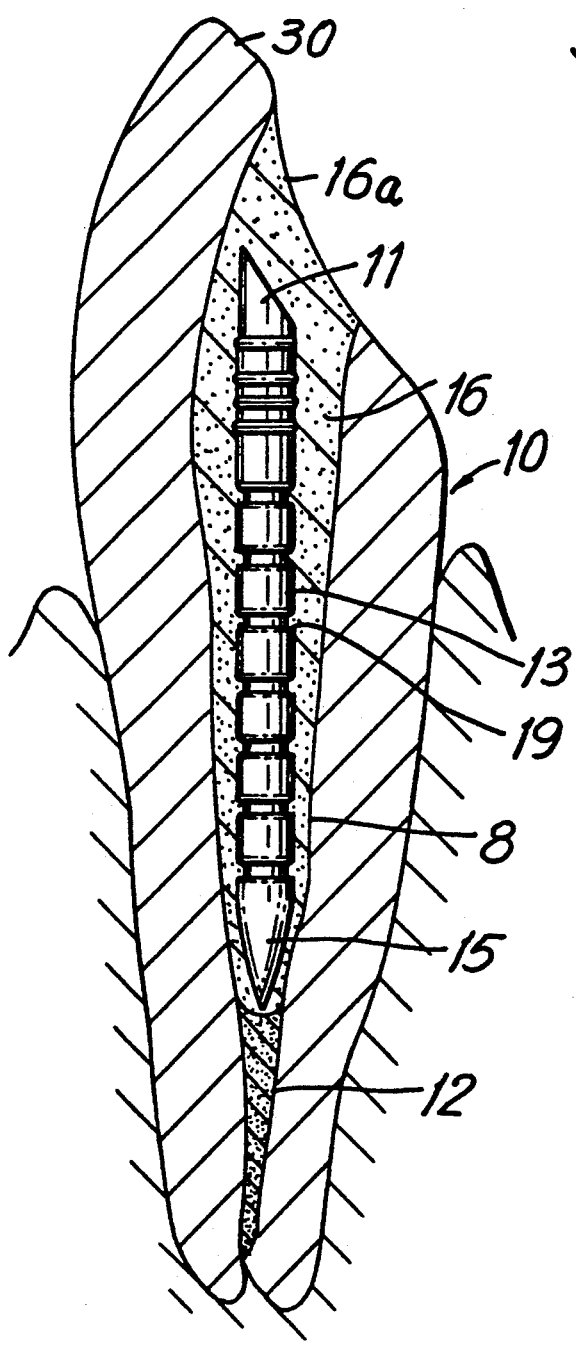
FIG. 1 is an elevation side cross-section view of a healthy obturated tooth reinforced using one embodiment of the flexible grooved, light-transmitting post of the present invention.
Figure 2:
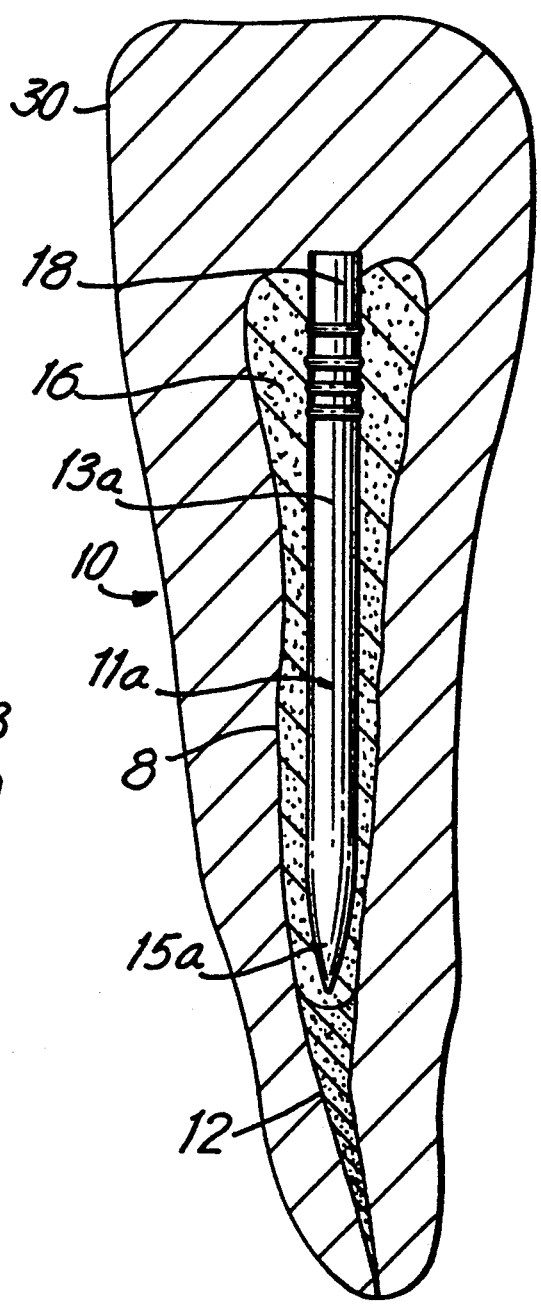
FIG. 2 is an elevation lingual cross-section view of a healthy obturated tooth being reinforced using one embodiment of the flexible smooth sided, light-transmitting post of the present invention.
Figure 3:
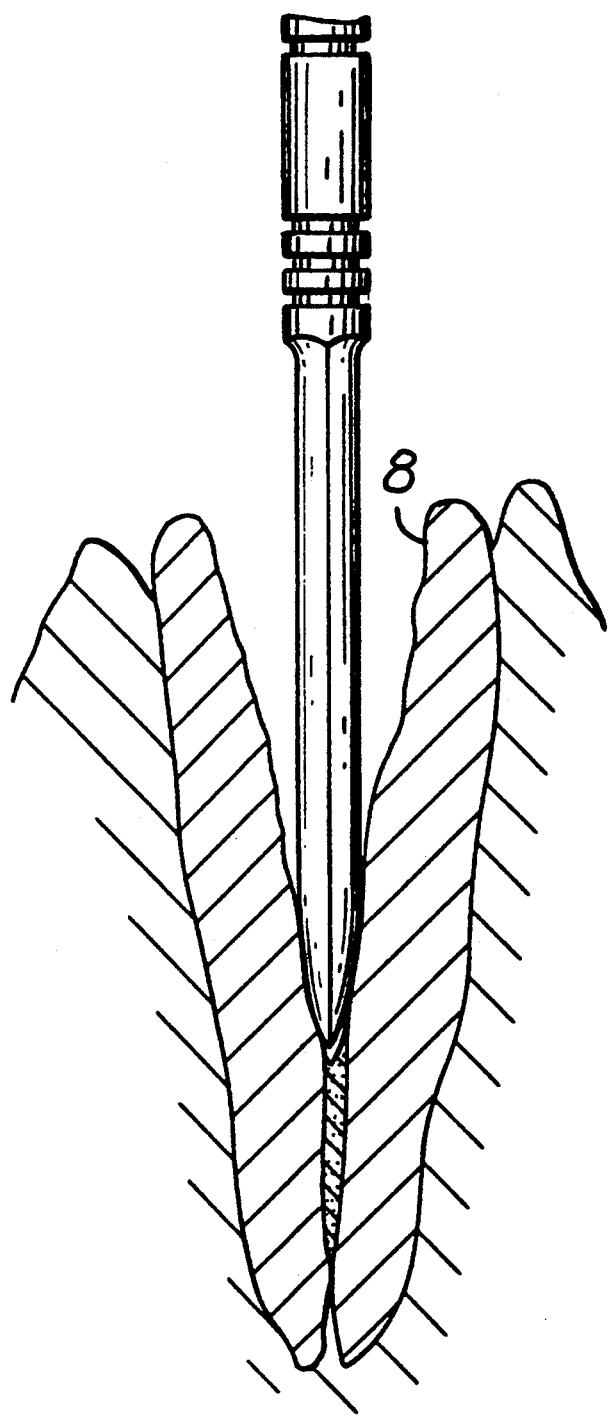
FIG. 3 is an elevation cross-section view of a tooth being reamed out to remove diseased tooth tissue and thus widen the root canal.
Figure 4:
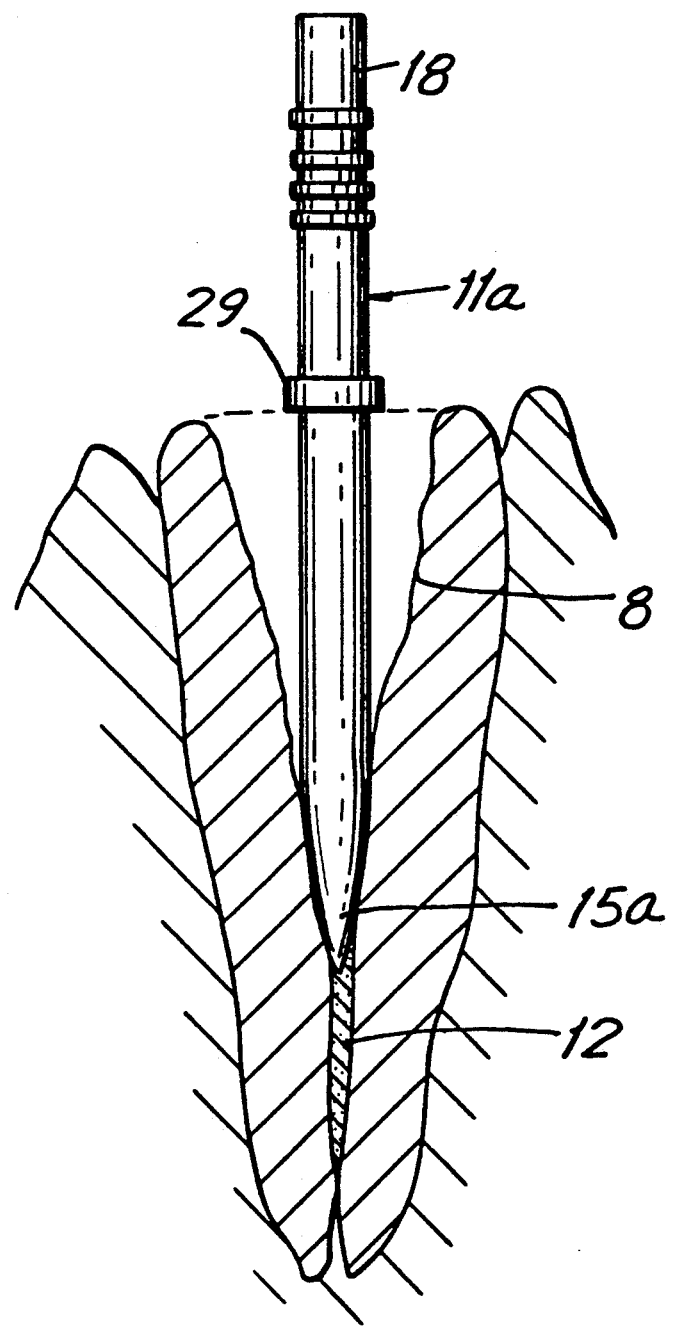
FIG. 4 is an elevation cross-section view showing a bored out root with a post centered in accordance with this invention, before being cemented in place with composite material.

Referring to FIG. 1, in an otherwise whole tooth 10, from which a damaged nerve has been removed, the root canal has been reamed in accordance with the usual technique, using a thin reamer tool, because there was little or no diseased root material. The apical portion has been filled with gutta percha 12, and the tooth rebored to smooth and define the canal immediately above the gutta percha 12,. to a desired convergent profile. Generally, the depth of the gutta percha 12 should be at least about 4 mm. A combined post tool and curing element 11 is inserted into the canal so as to fit snugly at the bottom, contacting the gutta percha, and the tooth canal wall is sealed by forming a casement 16 using a composite filler and a crown amalgam seal 16a. The grooved post 11 comprises a generally cylindrical shank 13, having a first bullet-shaped end portion 15, which has a profile substantially matching that of the drilling end of the reamer tool, and of the reamed out bottom of the canal.

As shown in FIGS. 2, and 4–6, a plastic post 11a was inserted into the reamed canal 8, such that the converging bullet-shaped end 15a fits in the interior portion of the tooth canal 8, immediately above and in contact with the gutta percha 12, but surrounded by an annular layer of the composite filler 16, except where the post touches the gutta percha; thus not closing off the apex. The post 11a is marked by a marker stop 29 to determine the depth of the root. The post 11a is then withdrawn, and a curable filling material, or composite 16a, is placed into the open tooth canal 8, and the post 11 is then pressed back into the canal until the marker 29 is level with the tooth surface, and the poet's bullet end 15a is again pressed against the bottom of the bore abutting the gutta percha sealant 12. Light is directed over the outer end of the post 11a (preferably using an optical hood connector 31, joining the light source 32 to the post 11), trans-illuminating the cement in the canal; this initiates curing of the composite, and thus forming a casement annulus over the walls 8.

The open top access into the tooth canal, in the otherwise intact coronal surface 30, is then filled and capped in the usual manner; it is usually necessary, first, to trim the outer end 18 of the post 11, so that it is below the tooth surface 30, allowing space for sealing and securely capping the opening. It must be noted that the preliminary processing views of FIGS. 3-7, discussed above, actually show a flared canal; however, the process steps are the same as described above for the whole, young tooth, except that the canal is not excessively widened and a plastic post is left in place, without the need for a prosthesis. Preferably, for a whole, young tooth, the plastic post 11, originally used, is grooved, as shown in FIG. 1, along its shank 13, to strengthen the retention in the canal and to improve curing using light.

Figure 10:
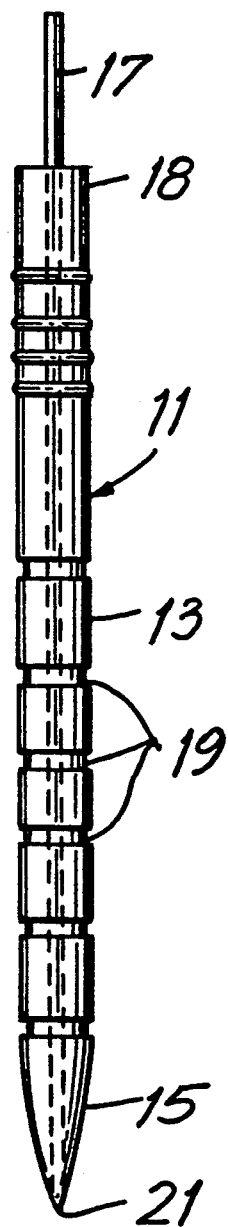
FIG. 10 is an elevation cross-section view of the root of FIG. 4, onto which a crown has been mounted in accordance with this invention
Figure 11:
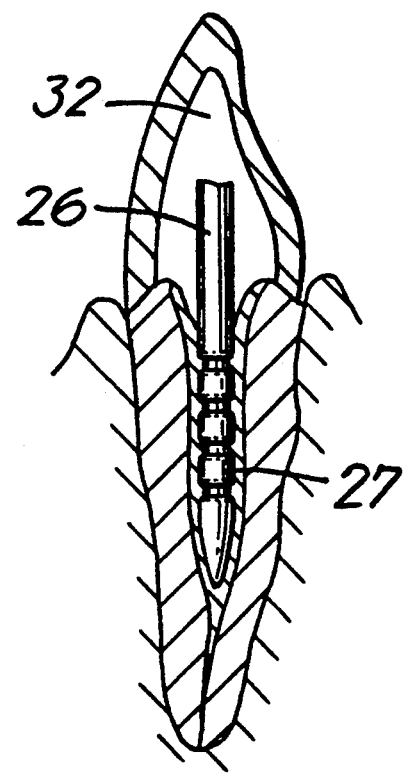
FIG. 11 is a plan view, from the rounded end, of a grooved plastic dental post of this invention, having a substantially circular cross-section.

In the post embodiment shown in FIG. 10, the tool post 11 has a central longitudinal channel extending fully along the central axis of the post, and an optical fiber rod 17, slidably positioned within the central bore and extending from the outer end 18, and into the convergent front tip 15 of the post; the fiber rod 17 can be connected at its outer end to a source of light of a suitable wavelength to cause the curing of the composite material. The rod 17 can be left behind in the canal, when the post is removed, and the curable composite packed around the rod 17; when the post is pressed back in, the rod serves to center the tool post within the tooth bore.

Figure 7:
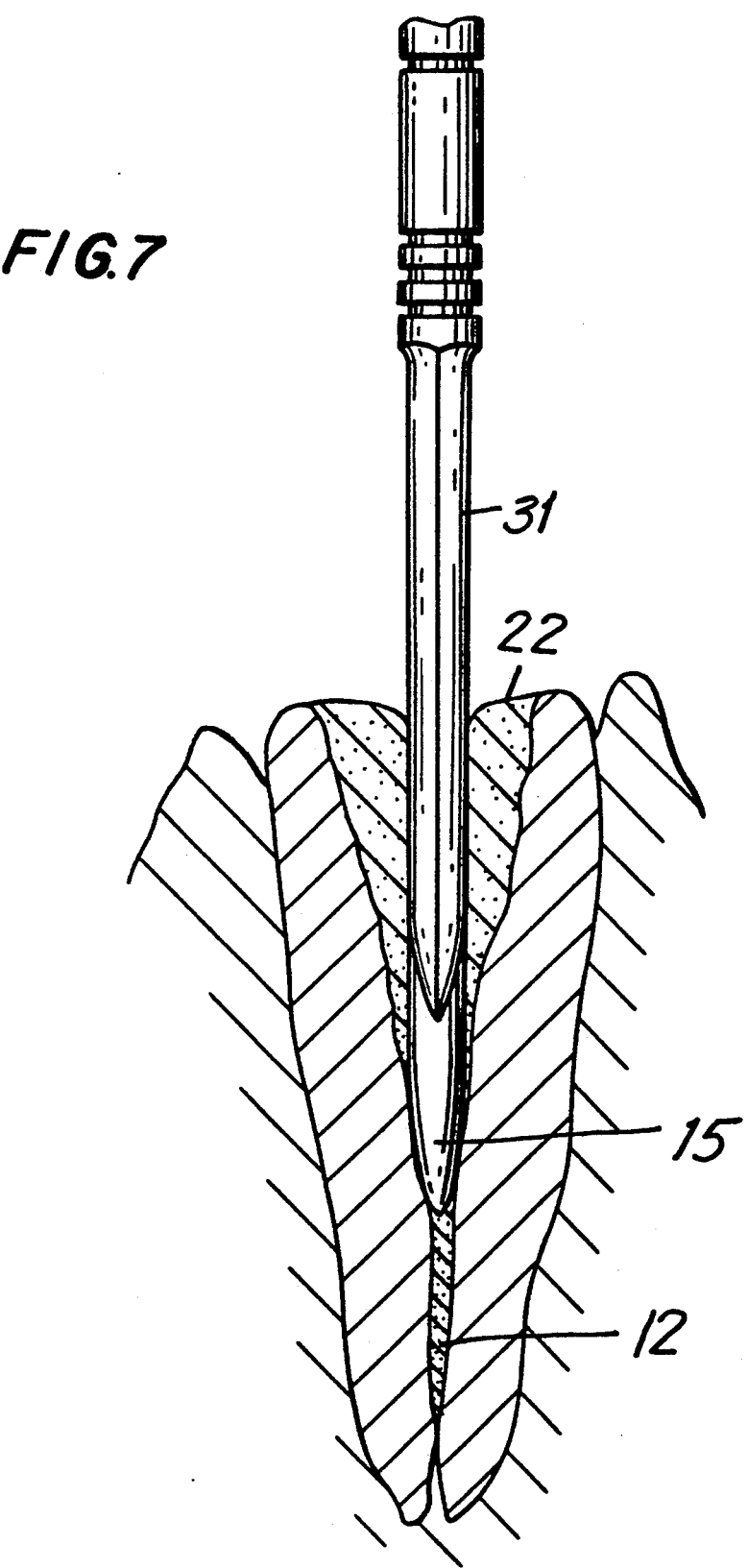
FIG. 7 is an elevation cross-section view of the tooth of FIG. 6, from which the curing post is being removed, in accordance with this invention.

An advantage of the embodiment of this invention as shown in FIG. 1, is to simplify any future access to the root apex, by eliminating the need for drilling through a cured, hard composite material blocking the innermost portion of the canal. By blocking the curable composite filler from completely filing the root canal, it is relatively easy to reopen the canal to perform subsequent endodontic procedures; for example, as is shown in FIG. 7, by using a regular reamer tool the post 11 and the gutta percha can be easily removed. Drilling out the top sealing layer 16a, covering over the plastic post, by using a diamond burr, and then drilling out the plastic post 11, using a simple reamer tool, is a relatively easy and safe process, if endodontic retreatment needs to be performed at a later date.

As shown, the plastic post is formed of a physiologically inert, transparent, or optically conductive, material, such as a polycarbonate (e.g., Lexan), or other FDA-approved material having the necessary structural, and preferably, optical properties. Preferably there can be a plurality of circumferential grooves 19 formed in the shank surface, spaced along the shank 13. The circumferential groove surfaces 19 act to concentrate the light at the groove apices, and to aid in retaining the post when used as a semi-permanent replacement, as in FIG. 1.

The plastic post is preferably somewhat flexible, so that it can negotiate the curved entrance to the canal, if needed, and should be of a lower hardness than the surrounding composite material, to provide a cushioning effect and to reinforce the annular composite casement bracing the bore.

In addition, preferably, the lower convergent end 15 of the post can be formed such that the minimum radius of curvature of the tip end is not greater than about 0.06 min., and most preferably is in the range of from about 0.03 to about 0.04 min. Concentrated light is radiated from the transparent bullet-shaped end tip, which can be utilized efficiently by intermittently moving the fiber rod into and along the central channel to initially cure the composite, and then very slowly, or intermittently, moving the post along the length of the canal to illuminate the entire length of the interior surface of the composite to ensure complete hardening.

The composite filler material can be cured by a variety of methods, including the use of a mixture containing an auto-curing agent, which will cure by itself, within a short period of time after being mixed. Most preferably, the composite material is light curable, as described above, and thus can be cured by the passage of light of the desired frequency, through the light-transmitting tool post 11. When an auto-curing cement is used, the post 11 need not be light-conducting, but preferably remains transparent to X-rays, unlike metal posts, to permit an unobstructed view of the canal without opening of the canal and removal of the post. The concentrated light emitted from the lower convergent end 15 of the tool post 11, is the most intense, especially for the smooth shank tool, and thus hastens the curing of even the lowermost portion of the light-curable composite material.

In another preferred embodiment, the end tip 21 of the rod 17, which is seated against a lower portion of the tooth canal, can be formed of an optically non-transmitting, reflective material, which will reflect light back upwardly along the rod 19 and outwardly through the circumference of the tool post 11.

The first advantage of the present invention is to provide a means of reinforcing an otherwise whole, healthy, well-embedded tooth, from which the nerve has been removed, in order to maintain the structural and functional integrity of the tooth. In that preferred, embodiment (FIG. 1), the composite filler material works together with the plastic tool post 11 to provide sufficient resilience to absorb stress on the tooth and root during function and thus reduce the possibility of further strain on the tooth, resisting the frequently encountered split roots. Suitable composite material formulated to act as a somewhat resilient, impact shock absorber, would maintain long-term usefulness for otherwise healthy, embedded roots in the supporting bone structure. Examples of such resilient composite materials, include the presently commonly used materials, but containing higher proportions of commony used filler particles.

To further improve the resilience of the composite material, there can also be provided a reinforcing mesh wrapped around the post 11, which becomes embedded in the composite material. The mesh can be formed of, e.g., a fluorocarbonate polymer, such as Teflon, or a rust-free metal, such as stainless steel or the usual gold or silver alloy compositions for the best function.

Figure 8:
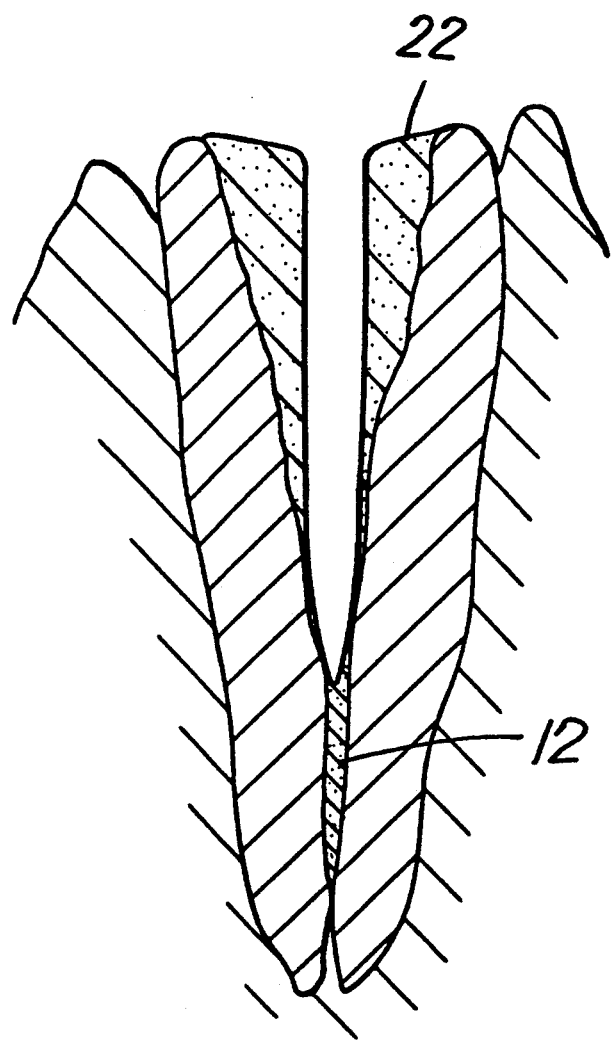
FIG. 8 is an elevation cross-section view of the tooth of FIG. 7, from which the curing post has been removed, leaving an annular casement, in accordance with this invention.
Figure 9:
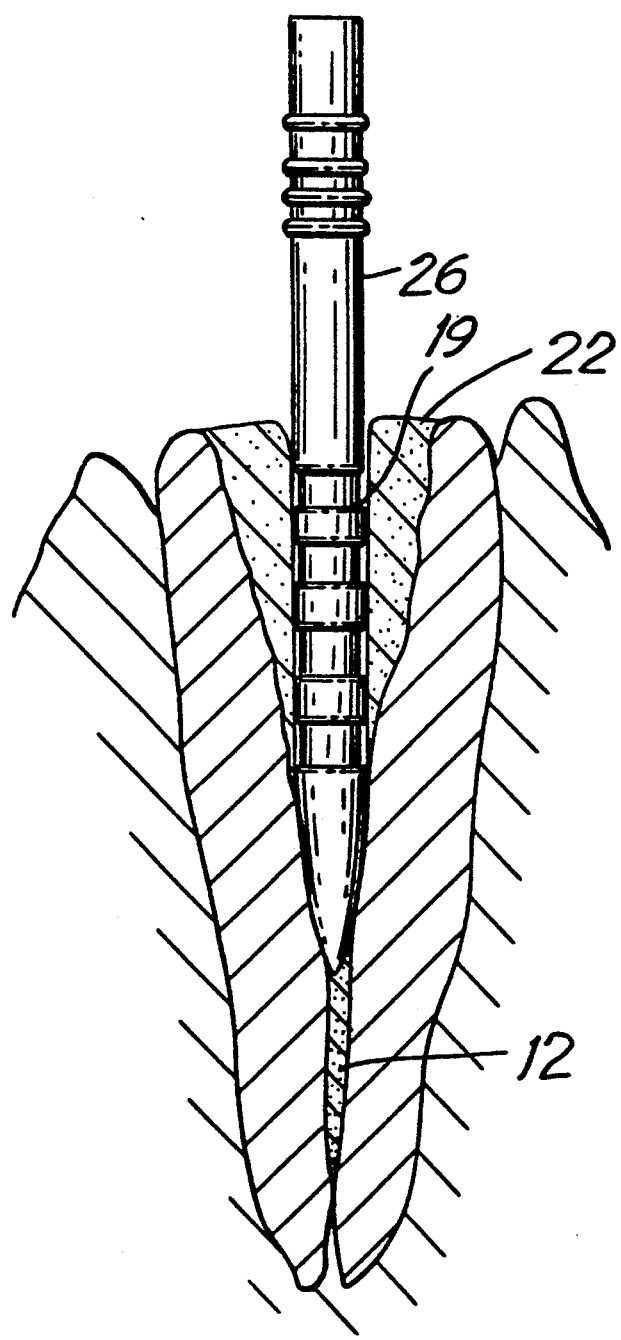
FIG. 9 is an elevation cross-section view of the tooth of FIG. 8, in which a grooved post has replaced the smooth post in the annular casement, in accordance with this invention.

This invention is also of special use in circumstances, such as shown by FIGS. 3–9, where the interior surface of the tooth canal 8 was severely excavated, resulting in a flared canal, and often leaving only a very thin root wall; such removal may take place during the original treatment, such as in FIG. 1, or after a retreatment. In either case, a severely widened, or flared, canal results in a poor prognosis for the tooth, even if the tooth was securely anchored in the jawbone. However, with this invention, it is possible to internally reinforce and brace the walls while simultaneously creating maximum length, desirably sized parallel canal walls for immediate or future installation of a stronger metal post. Following the procedure exemplified by FIGS. 3–8, an appropriately sized (lubricated or insulated) post 11 is secured in place to its maximum depth in the canal; and after the composite has been cured, the post can often be withdrawn with a firm twisting motion, or alternately may be readily drilled out using the same size reamer (as shown by FIG. 7), leaving an open canal with an annular composite casement 22, as shown in FIG. 8.

Figure 5:
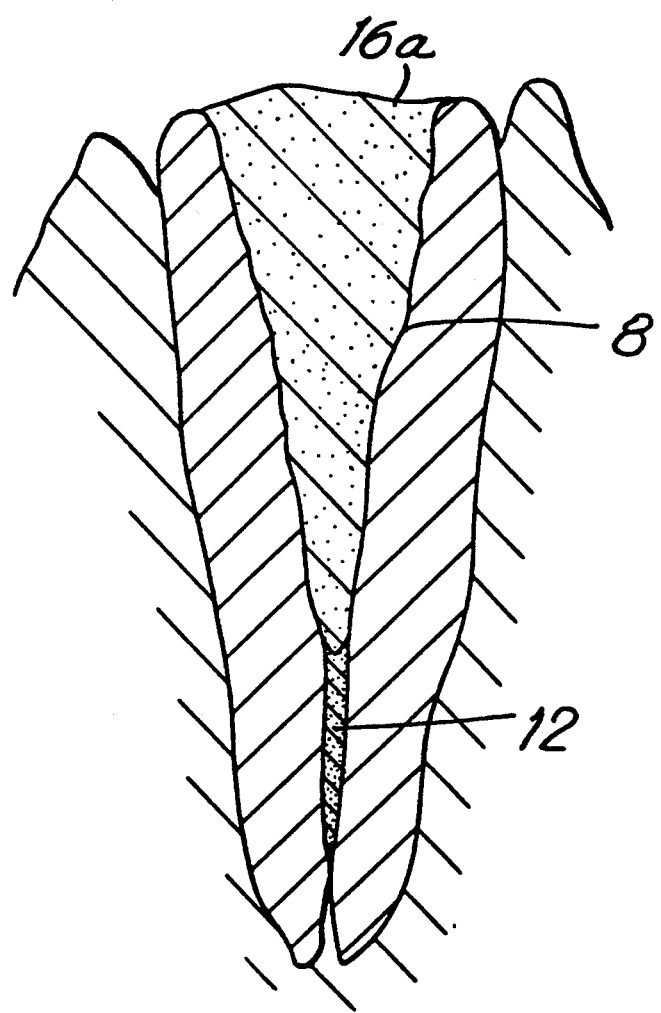
FIG. 5 is an elevation cross-section view of the tooth of FIG. 4, from which the post has been removed and uncured composite filler emplaced.
Figure 6:
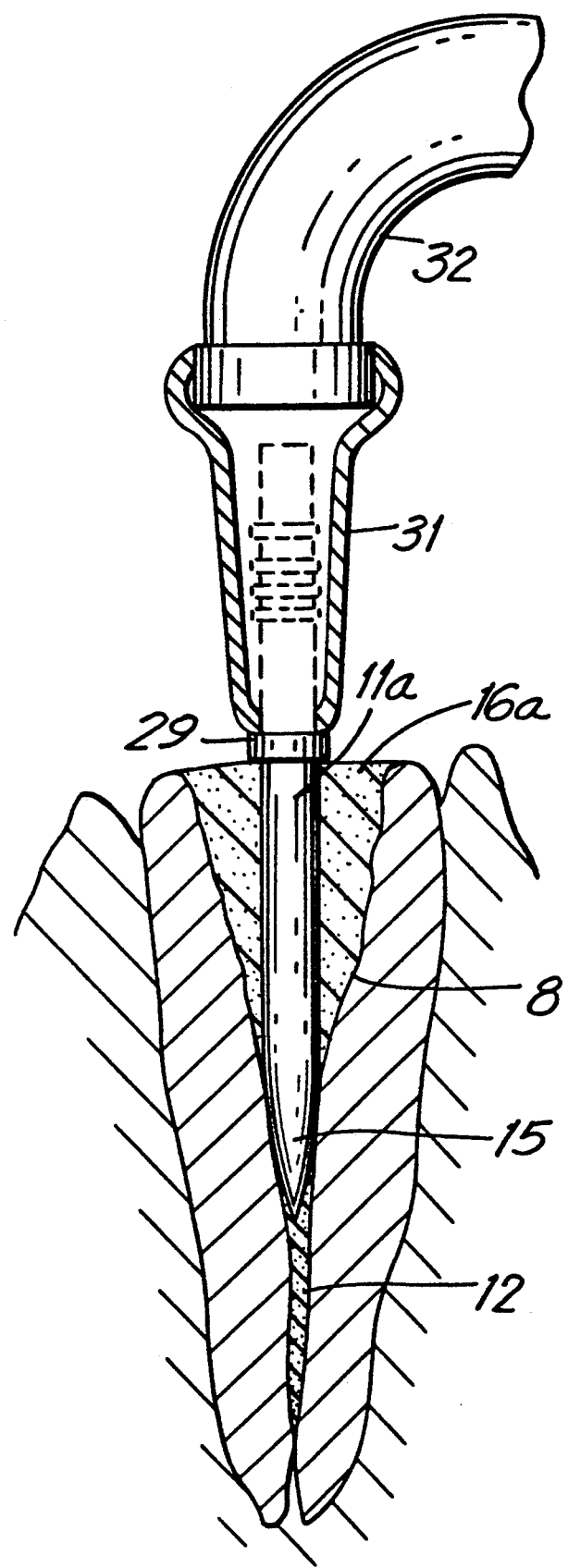
FIG. 6 is an elevation cross-section view of the tooth of FIG. 5, into which the post has been replaced and the tooth is further prepared for curing of the filler in accordance with this invention.

In either case, the casemented canal, as shown by FIG. 8, is preferably then routed out using, e.g., the reamer-router tool 31 of U.S. Pat. No. 4,990,088, to form minute retentive and anti-rotational indents in the internal circumferential surface of the annulus 22 of the cured composite. A correspondingly sized, but structurally stronger, grooved post 26 is then inserted and cemented in place, as shown by FIG. 5. The structurally stronger post 26 is preferably made of a metal acceptable for such use. The composite, and/or luting materials, can first be further cured by a more direct application of light, transmitted through a smaller, preferably grooved, plastic post that is slidable in the canal, directing the light in incremental stages through its entire length.

A metal dental post 26, of a usual type, can be emplaced in a casemented canal prepared according to this invention and shaped, so that when cast, a post core can be cemented, or otherwise secured, and used as a foundation of a coronal restoration 32. The permanent metal post 26 can be passively cemented into the casemented canal 8, or can be actively installed, utilizing a slightly larger post with screw threads to anchor the post directly into the casement walls 22 of the canal; the so-called active screw threads biting directly into the composite casement walls 22.

The dental posts of this invention should be of the usual size useful for dentistry. For example, the maximum post diameters should be no greater than about 1.9 ram, and preferably in the range of from about 1 to about 1.9 mm. Although the posts can be substantially circular in cross-section, if it is desired that they cannot rotate within the canal, the canal and the posts can be formed with an oval cross-section, or with a polygonal cross-section. The length of the posts should preferably be no greater than about 20 mm, and are preferably in the range of from about 8 to about 15 mm. The length of the convergent end portion of the plastic posts is preferably not greater than about 10 mm, and preferably in the range of from about 4 to about 8 mm, and is determined by the length of the tooth root and the amount of natural tooth remaining. The grooves are preferably separated by at least about 0.1 mm, and preferably at least about 0.3 mm.

The embodiments of the present invention herein described and claimed are presented merely as examples of the present invention. Other embodiments coming within the scope of the present invention will readily suggest themselves to those skilled in the art, and shall be deemed to come within the scope of the appended claims.

The patentable embodiments of the invention which are claimed are as follows:

1. A method of reinforcing a tooth from which its nerve has been removed, and its canal has been cleaned to remove all diseased tissue, the method comprising: filling at least the apical portion of the canal with a soft resilient material; reaming out the canal with a reamer to form a converging section at its innermost portion, to an end of minimum diameter at the edge of the portion filled with the soft resilient material, so that the innermost portion matches the profile of the cutting end of the reamer; inserting a tool post into the bored out canal, the tool post being formed of a relatively flexible material, and having a substantially cylindrical shank with a diameter smaller than that of the canal, and an inwardly tapering, or convergent, first end, also similar to the profile of the cutting end of the reamer, such that the convergent first end seats against the convergent surface of the reamed out canal; adding a curable composite to fill the canal, surrounding the post, and permitting the composite to cure; the post being formed of physiologically inert, material which is sufficiently flexible that it can follow the curvature of the canal.

2. The method of claim 1 wherein the tool post is formed of optically transmitting material and the composite is light curable, and wherein the method further comprises passing light through the post to cure the composite.

3. The method of claim 2 wherein the tool post further comprises an internal circumferential surface defining a channel extending substantially axially longitudinally through the post, and a relatively movable rod extending into and through the axial channel and the convergent first end, so as to contact the soft resilient filler material; and wherein the tool post is initially moved out of the canal without moving the rod from contact against the soft resilient material; and wherein the post is moved back into the canal by sliding along, and without moving, the rod, after the composite is placed into the canal.

4. The method of claim 3 wherein the innermost end of the rod extending into the convergent portion of the tool post is formed of a reflective, optically non-transmitting material.

5. The method of claim 2 wherein the tool post is formed of a material which is optically transparent to the frequency of light needed to cure the composite and wherein the post further comprises circumferential groove portions spaced along the circumferential surface of the tool post shank.

6. A method of reinforcing a tooth from which its nerve has been removed, and its canal has been cleaned to remove all diseased tissue and substantially straightened preparatory to forming a prosthetic crown or other prosthesis, the method comprising: filling at least the apical portion of the canal with a soft resilient material; reaming out the canal with a reamer to form a converging section at its innermost portion to an end of minimum diameter at the edge of the portion filled with the soft resilient material, so that the innermost portion matches the profile of the cutting end of the reamer; inserting a tool post into the bored out canal, the tool post being formed of a relatively resilient material, and having a substantially cylindrical shank with a diameter smaller than that of the canal, and an inwardly tapering, or convergent, first end, also similar to the profile of the cutting end of the reamer, such that the convergent first end seats against the convergent surface of the reamed out canal; adding a curable composite to substantially fill the canal; surrounding the post, and permitting the composite to cure; the post being formed of physiologically inert, material; removing the post from the canal, leaving an annular ring of cured composite material; replacing the post with a matching post formed of a structurally stronger material capable of supporting a dental prosthesis; and cementing the matching post into the canal.

7. The method of claim 6, wherein the matching post further comprises an anchor portion extending out of the canal; and wherein the method further comprises forming the anchor portion to act as a support for a suitable prosthesis.

8. A dental tool post for reinforcing an obturated tooth and root, the dental tool post comprising a substantially cylindrical shank portion and an inwardly tapering, or convergent, first end, a plurality of circumferential grooves being formed in the surface of the shank portion of the tool post, and the post being formed of a physiologically inert, optically transmitting relatively flexible polymeric material.

9. The tool post of claim 8, wherein the convergent first end of the post includes a transverse cross-section having a diameter not greater than the diameter of a natural root canal.

10. The dental tool post of claim 8, wherein the tool post is sufficiently flexible to follow the natural curvature of a natural root canal.

11. A dental tool post for reinforcing an obturated tooth and root, the dental tool post comprising a substantially cylindrical shank portion and an inwardly tapering, or convergent, first end, a plurality of circumferential grooves being formed in the surface of the shank portion of the t post, and the post being formed of a physiologically inert optically transmitting relatively flexible polymeric material, and an internal circumferential surface defining a channel extending substantially axially longitudinally through the post, and a relatively moveable rod extending into and through the axial channel and beyond the convergent first end, the central rod being an optical fiber material.

12. The tool post of claim 11, further comprising a reflective, non-transmitting surface formed on the first end of the optical rod.

* * * * *